United States Patent [19]

Jen et al.

[11] 3,952,101
[45] Apr. 20, 1976

[54] α-AMINOMETHYL-5-HYDROXY-2-PYRIDINEMETHANOLS

[75] Inventors: Timothy Yu-Wen Jen, Broomall, Pa.; Carl Kaiser, Haddon Heights, N.J.

[73] Assignee: SmithKline Corporation, Philadelphia, Pa.

[22] Filed: Apr. 14, 1975

[21] Appl. No.: 568,079

[52] U.S. Cl. ........................ 424/263; 260/294.8 F; 260/294.8 R; 260/295 S; 260/296 R; 260/296 B; 260/296 AE
[51] Int. Cl.² ................. C07D 213/38; A61K 31/44
[58] Field of Search ......... 260/296 R, 295 S, 296 B, 260/296 AE, 294.8 F; 424/263

[56] References Cited
UNITED STATES PATENTS

| | | | |
|---|---|---|---|
| 3,558,642 | 1/1971 | Hartley et al. | 260/296 R |
| 3,700,681 | 10/1972 | Barth | 260/296 R |

Primary Examiner—Henry R. Jiles
Assistant Examiner—Robert W. Ramsuer
Attorney, Agent, or Firm—Richard D. Foggio; William H. Edgerton

[57] ABSTRACT

α-Aminomethyl-5-hydroxy-2-pyridinemethanols having β-adrenergic stimulant activity, particularly as selective bronchodilators, are prepared generally from a 2-pyridine-carboxaldehyde by reaction with an appropriate isocyanide, via an amide intermediate followed by reduction to an amine and finally catalytic hydrogenation to remove benzyl protective groups.

13 Claims, No Drawings

α-AMINO METHYL-5-HYDROXY-2-PYRIDINEMETHANOLS

This invention relates to novel α-aminomethyl-5-hydroxy-2-pyridinemethanols which have useful pharmacodynamic activity. More specifically the compounds of this invention have utility as β-adrenergic stimulants with relatively greater activity on respiratory smooth muscle than on cardiac muscle. Therefore these compounds have direct bronchodilator action with minimal cardiac stimulation as demonstrated in standard pharmacological test procedures.

Two in vitro test systems used for determining selective β-stimulant activity are: (1) effect on spontaneous tone of guinea pig tracheal chain preparations as a measure of β-stimulant (direct relaxant) effect on airway smooth muscle, and (2) effect on rate of spontaneously beating right atria of the guinea pig as a measure of β-stimulant effect on cardiac muscle. The compounds of this invention have selective bronchodilating properties since they are active in (1) above at a dose lower than is required in (2) above resulting in a positive separation ratio.

The compounds of this invention are represented by the following general structural formula:

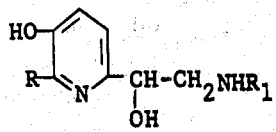

FORMULA I in which:

R represents hydrogen, methyl or methanesulfonylmethyl;

$R_1$ represents a branched chain lower alkyl group of from 3 to 5 carbon atoms, a cycloalkyl or cycloalkylmethyl group, the cycloalkyl moiety having from 3 to 6 carbon atoms, or

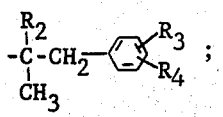

$R_2$ represents hydrogen or methyl; and $R_3$ and $R_4$ represent hydrogen, hydroxy, methoxy or, taken together in adjacent positions, methylenedioxy.

Preferred compounds of this invention are represented by formula I above when R is methanesulfonylmethyl; and $R_1$ is isopropyl, t-butyl, cyclopropyl, cyclopentyl, 4-hydroxyphenylisopropyl or 3,4-methylenedioxyphenylisopropyl.

The compounds of this invention may be used in the form of a pharmaceutically acceptable acid addition salt having the utility of the free base. Such salts, prepared by methods well known to the art, are formed with both inroganic or organic acids, for example: maleic, fumaric, benzoic, ascorbic, pamoic, succinic, bismethylenesalicylic, methanesulfonic, ethanedisulfonic, acetic, oxalic, propionic, tartaric, salicylic, citric, gluconic, aspartic, stearic, palmitic, itaconic, glycolic, p-amino-benzoic, glutamic, benzenesulfonic, hydrochloric, hydrobromic, sulfuric, cyclohexylsulfamic, phosphoric and nitric acids.

Compounds of this invention may be present as d, l optical isomers. Resolution of optical isomers may be conveniently accomplished by fractional crystallization of their salts with optically active acids such as, for example, tartaric, camphor-10-sulfonic, O,O-dibenzoyltartaric, O,O-di-(p-toluoyl)tartaric, menthyloxyacetic, camphoric, or 2-pyrrolidone-5-carboxylic acids or N-acetyltryptophane from appropriate solvents. Unless otherwise specified in the claims, it is intended to include all isomers whether separated or mixtures thereof.

The compounds of this invention are prepared as shown in the following sequence of reactions:

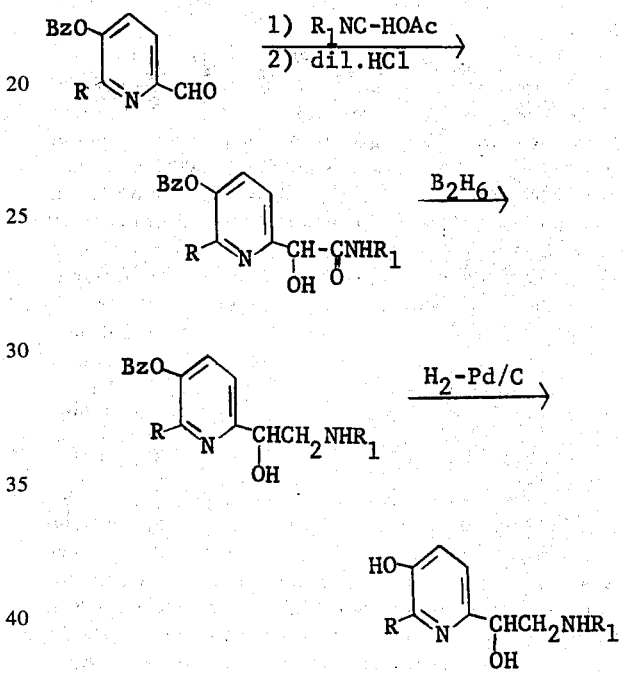

in which Bz is benzyl and R and $R_1$ are as defined in formula I. Thus, as shown above, a pyridinecarboxaldehyde is treated with an isocyanide in the presence of acetic acid to afford the acetoxy amide as an intermediate which is hydrolyzed by dilute acid to give the hydroxy amide. The required isocyanide is prepared by treatment of an $R_1$ substituted formamide with phosphorus oxychloride and pyridine in refluxing chloroform.

Reduction of the hydroxy amide is accomplished with diborane in an unreactive organic solvent such as tetrahydrofuran and catalytic hydrogenation, preferably with palladium-on-carbon, to remove the 5-benzyl group (as well as any other benzyl protective groups present in $R_1$) gives the desired product.

The pyridinecarboxaldehydes used as starting materials herein are prepared from known compounds by methods available in the art as described more fully in the examples. These useful aldehydes form a part of the invention.

A preferred compound of this invention is α-(t-butylaminomethyl)-5-hydroxy-6-methanesulfonylmethyl-2-pyridinemethanol which relaxes the spontaneous tone of guinea pig tracheal ring preparation at an $ED_{50}$ of 0.0088 mcg/ml while only increasing by 13% the rate of contraction of guinea pig right atria at a dose of 30.0 mcg/ml. These activities give an absolute separation ratio which is greater than 6800 times more selective than the corresponding activity of d,l-isoproterenol (absolute separation ratio = 0.5) in similar in vitro preparations.

U.S. Pat. Nos. 3,700,681 and 3,763,173 disclose α-aminomethyl-5-hydroxy-2-pyridinemethanols having a 6-hydroxymethyl substituent as bronchodilators; U.S. Pat. NO. 3,558,642 discloses 2-halo-α-aminomethylpyridinemethanols as β-adrenergic blockers or stimulants; O. E. Schultz et al. *Arch. Pharm.* 305:248–53, 1972 discloses α-aminomethyl-4-pyridinemethanols as β-receptor blockers; and C. T. Gnewuch and H. L. Friedman, *J. Med. Chem.* 15:1321–4, 1972 discloses α-aminomethyl-2-and 3-pyridinemethanols as β-receptor agonists.

The compounds of this invention may be administered orally or parenterally in conventional dosage unit forms such as tablets, capsules, injectables or the like, by incorporating the appropriate dose of a compound of formula I, with carriers according to accepted pharmaceutical practices. Preferably a compound or an acid addition salt thereof is administered orally to an animal organism in a tablet or capsule comprising an amount sufficient to produce β-adrenergic stimulant activity. Each dosage unit will contain the active medicament in an amount of about 5 mg. to about 250 mg., preferably about 10 mg. to about 150 mg. Advantageously equal doses will be administered 2 to 4 times daily with the daily dosage regimen being about 10 mg. to about 1000 mg., preferably about 20 mg. to about 600 mg.

The pharmaceutical carrier employed may be, for example, either a solid or liquid. Exemplary of solid carriers are lactose, terra laba, sucrose, talc, gelatin, agar, pectin, acacia, magnesium stearate, stearic acid and the like. Exemplary of liquid carriers are syrup, peanut oil, olive oil, water and the like. Similarly the carrier or diluent can include any time delay material well known to the art, such as glyceryl monostearate or glyceryl distearate alone or with a wax.

A wide variety of pharmaceutical forms can be employed. Thus, if a solid carrier is used the preparation can be tableted, placed in a hard gelatin capsule in powder or pellet form, or in the form of a troche or lozenge. The amount of solid carrier will vary widely but preferably will be about 1 g. If a liquid carrier is used, the preparation will be in the form of a syrup, emulsion, soft gelatin capsule, sterile injectable liquid such as an ampul, or an aqueous or nonaqueous liquid suspension.

Of particular applicability is an aerosol dispensing system wherein the active medicament is incorporated with Freon (fluorohydrocarbon) or other inert propellant in an aerosol container. Such aerosol system will deliver a metered dose of about 50 mcg. to about 500 mcg., administered once or twice at a time as needed.

The foregoing is a general description of how to prepare the compounds of this invention. The following examples illustrate the preparation of specific compounds having β-adrenergic stimulant activity. However this should not be construed as a limitation of the invention since appropriate variations in the starting materials will produce other products set forth hereinabove.

PREPARATIONS

A.
5-Benzyloxy-6-methanesulfonylmethyl-2-pyridinecarboxaldehyde.

To a stirred solution of 5-benzyloxy-6-hydroxymethyl-2-pyridinecarboxaldehyde (5.86 g., 0.0241 mol) in 100 ml. of ethyl acetate is added 4.056 g. (0.0265 mol) of phosphorus oxychloride and the mixture is refluxed for 20 minutes. Additional phosphorus oxychloride (0.4 ml.) is introduced and the mixture is heated further for 30 minutes. The reaction mixture is cooled, diluted with ether and then washed with 5% sodium bicarbonate solution and brine. The ethereal solution is dried, treated with charcoal, filtered and evaporated to leave an oil which crystallizes to give 5-benzyloxy-6-chloromethyl-2-pyridinecarboxaldehyde, m.p. 72°–73°C.

A mixture of the above chloromethyl compound (2.65 g., 0.010 mol) in 120 ml. of 2-propanol and 13.5 g. of magnesium methylsulfinate (45% purity) in 120 ml. of water is refluxed for four hours. The 2-propanol is evaporated and the aqueous solution containing a precipitate is extracted with methylene chloride. Evaporation of the solvent gives 5-benzyloxy-6-methanesulfonylmethyl-2-pyridinecarboxaldehyde, m.p. 103°–104°C.

B. 5-Benzyloxy-2-pyridinecarboxaldehyde.

To a solution of sodium ethoxide prepared from 1.3 g. (0.0565 g.-atom) of sodium and 30 ml. of absolute ethanol is added a solution of 5-hydroxy-2-methylpyridine (5.0 g., 0.0458 mol) in 15 ml. of ethanol, followed by 8.6 g. (0.05 mol) of benzyl bromide. The mixture is refluxed for three hours, poured into 150 ml. of water and extracted with ether. The extract is dried and then treated with ethereal hydrogen chloride. The hydrochloride salt is dissolved in water and the aqueous solution is washed with ether, basified and extracted with ether. The dried extract is treated with charcoal and evaporated to give 5-benzyloxy-2-methylpyridine as a pale yellow oil.

A solution of 38.1 g. (0.1915 mol) of 5-benzyloxy-2-methylpyridine in 1 l. of chloroform is treated at 25°C. with 42.7 g. of 85% m-chloroperbenzoic acid. Ater one hour the solution is washed with 5% aqueous sodium carbonate, water, dried and evaporated to give 5-benzyloxy-2-methylpyridine-N-oxide, m.p. 87°–89°C.

To 80 ml. of acetic anhydride stirred at 135°C. is added slowly 39.8 g. (0.185 mol) of the above N-oxide. The solution is stirred at this temperature for 30 minutes and then poured into 500 ml. of ice-water. After stirring the mixture for two hours it is extracted with a mixture of ethyl acetate and ether. The extract is washed with water, dried and evaporated to dryness. The residue is passed through an alumina column with ether as the eluent. Evaporation of the first fraction yields 2-acetoxymethyl-5-benzyloxypyridine as an oil.

A solution of 25.0 g. (0.098 mol) of the above acetoxymethyl compound in 200 ml. of ethanol and 50 ml. of water is treated with 7.0 g. of sodium hydroxide and refluxed for four hours. The solution is evaporated and the residue is taken up in a mixture of ethyl acetate and ether. This solution is washed with water, dried and evaporated to dryness, leaving the solid 5-benzyloxy-2-hydroxymethylpyridine, m.p. 66°–68°C.

A well-stirred mixture of 14.0 g. (0.065 mol) of the above hydroxymethyl compound and 140 g. of activated manganese dioxide in 700 ml. of chloroform is refluxed for five minutes. The manganese dioxide is filtered and the solvent evaporated to give 5-benzyloxy-2-pyridinecarboxaldehyde, m.p. 68°–70°C.

C. 5-Benzyloxy-6-methyl-2-pyridinecarboxaldehyde.

A mixture of 27.2 g. (0.25 mol) of 3-hydroxy-2-methylpyridine, 100 ml. of 10% sodium hydroxide in 75 ml. of water and 22.5 ml. (0.25 mol) of 40% formalin (aqueous methanolic formaldehyde solution) is refluxed for two hours. An additional amount of 40% formalin (22.5 ml.) is added and the reflux is continued for two hours. The mixture is acidified with acetic acid and the resulting precipitate is filtered and washed with acetone. The filtrate is evaporated to dryness and the residue is repeatedly extracted with hot acetone. The extract is dried, treated with charcoal and evaporated to give crude 3-hydroxy-6-hydroxymethyl-2-methylpyridine as a solid.

A stirred mixture of the above prepared pyridine (26 g., 0.187 mol), 7.5 g. (0.187 mol) of sodium hydroxide in 20 ml. of water and 32.0 g. (0.187 mol) of benzyl bromide in 400 ml. of acetone and 200 ml. of water is refluxed for five hours. The acetone is evaporated and the aqueous solution is extracted with ethyl acetate. The ethyl acetate solution is washed with 2% sodium hydroxide and extracted with 5% hydrochloric acid. The acidic solution is made alkaline with 10% sodium hydroxide and extracted with ethyl acetate. The extract is dried, treated with charcoal and evaporated. The residue in methanol is treated with ethereal hydrogen chloride to yield 3-benzyloxy-6-hydroxymethyl-2-methylpyridine hydrochloride.

A mixture of 19.4 g. (0.0846 mol) of 3-benzyloxy-6-hydroxymethyl-2-methylpyridine (liberated from the hydrochloride salt) and 100 g. of manganese dioxide in 800 ml. of chloroform is refluxed with vigorous stirring for three hours. The mixture is filtered and the chloroform is evaporated to give a yellow oil which is chromatographed on alumina, eluting with chloroform. The recovered material is purified through its hydrochloride salt and reconverted to the base, 5-benzyloxy-6-methyl-2-pyridinecarboxaldehyde, m.p. 62°–63°C.

EXAMPLE 1

A solution of 2.0 g. (0.0066 mol) of 5-benzyloxy-6-methanesulfonylmethyl-2-pyridinecarboxaldehyde in 50 ml. of chloroform is refluxed gently with 1.1 g. (0.013 mol) of t-butylisocyanide and 0.8 g. (0.013 mol) of acetic acid for three hours. The reaction mixture is washed with 5% sodium bicarbonate solution and the chloroform solution is evaporated to dryness. The residue is chromatographed on silica gel (40 g., packed with ether), eluted with ether and then methylene chloride which furnished upon evaporation 2[α-(N-t-butylamido)-acetoxymethyl]-5-benzyloxy-6-methanesulfonylmethylpyridine as an oil.

A solution of the above prepared pyridine (2.0 g.) in 20 ml. of methanol and 30 ml. of 1N hydrochloric acid is refluxed for one and one-half hours. The methanol is evaporated in vacuo, the aqueous solution is made alkaline with sodium hydroxide solution and then extracted with methylene chloride. The dried extract is evaporated to dryness to give 5-benzyloxy-α-(N-t-butylamido)-6-methanesulfonylmethyl-2-pyridinemethanol.

The above prepared amide (1.3 g., 0.0032 mol) in 30 ml. of tetrahydrofuran is refluxed with 20 ml. of a 1M tetrahydrofuran solution of diborane for one hour. The solvent is evaporated and the residue is treated with ice-water and 3N hydrochloric acid. The acidic solution is washed with ether and then made alkaline with 40% sodium hydroxide solution. This mixture is extracted repeatedly with ethyl acetate. The extract is washed with brine, dried and evaporated to dryness to leave a gum. Trituration with ether-hexane gives 5-benzyloxy-α-(t-butylaminomethyl)-6-methanesulfonylmethyl-2-pyridinemethanol, m.p. 117°–119°C.

The above compound (0.46 g., 0.0011 mol) in 30 ml. of anhydrous ethanol is hydrogenated with 0.5 g. of 10% palladium-on-carbon at 50 psi for 20 minutes. The catalyst is removed and the filtrate is evaporated to leave α-(t-butylaminomethyl)-5-hydroxy-6-methanesulfonylmethyl-2-pyridinemethanol. The latter (0.2 g., 0.662 mmol) in warm methanolic solution is treated with 0.043 mg. (0.37 mmol) of fumaric acid. Upon slow addition of ether to this solution and with cooling, the fumarate salt is obtained, m.p. 210°–212°C.

EXAMPLE 2

A solution of 4.22 g. (0.02 mol) of 5-benzyloxy-2-pyridinecarboxaldehyde in 100 ml. of chloroform is treated with 1.66 g. (0.04 mol) of t-butyl isocyanide and 2.40 g. (0.04 mol) of acetic acid and the solution is refluxed gently for five hours. The reaction mixture is washed with 5% sodium bicarbonate solution, dried and evaporated to dryness to give 2-[α-N-t-butylamido)-acetoxymethyl]-5-benzyloxypyridine.

The above prepared pyridine (4.0 g., 11.2 mmol) in 40 ml. of methanol, 40 ml. of water and 20 ml. of 10% hydrochloric acid is refluxed for one and one-half hours. The methanol is evaporated and the aqueous solution is basified, then extracted with ethyl acetate. The extract is washed with water, dried and evaporated to yield 5-benzyloxy-α-(N-t-butylamido)-2-pyridinemethanol, m.p. 71°–73°C.

To 45 ml. of a 1M solution of diborane in tetrahydrofuran is added a solution of the above amide (3.3 g., 10.5 mmol) in 100 ml. of tetrahydrofuran. The mixture is refluxed for two hours and the solvent evaporated. The residue is treated continuously with ice and 1N hydrochloric acid. This acidic solution is washed with ether, basified and extracted with ethyl acetate. The extract is dried, evaporated and the residual oil, dissolved in a small amount of ethanol, is treated with ethereal hydrogen chloride to precipitate the hydrochloride salt of 5-benzyloxy-α-(t-butylaminomethyl)-2-pyridinemethanol, m.p. 210°–212°C.

A solution of 600 mg. (2 mmol) of 5-benzyloxy-α-(N-t-butylaminomethyl)-2-pyridinemethanol (liberated from the hydrochloride salt) in 100 ml. of ethanol is hydrogenated over 600 mg. of 10% palladium-on-carbon at 50 psi for 10 minutes. The catalyst is filtered and ethanol evaporated to dryness. The residue is recrystallized from ethanol to give α-(t-butylaminomethyl)-5-hydroxy-2-pyridinemethanol, m.p. 163°–165°C.

EXAMPLE 3

A mixture of 4.8 g. (0.0212 mol) of 5-benzyloxy-6-methyl-2-pyridinecarboxaldehyde, 2.4 ml. (0.042 mol) of acetic acid and 2.08 g. (0.0251 mol) of t-butyl isocyanide in 75 ml. of chloroform is refluxed for two hours. An additional amount of t-butylisocyanide (1.0 g., 0.0121 mol) is added and the reflux is continued for five hours. The chloroform solution is washed with 5% sodium bicarbonate solution, dried and evaporated to dryness to give 2-[α-(N-t-butylamido)-acetoxymethyl]-5-benzyloxy-6-methylpyridine. A sample in methanol is treated with ethereal hydrogen chloride to give a hydrochloride salt, m.p. 135°–137°C.

A solution of 7.5 g. of the amide (free base) in dilute hydrochloric acid (4 ml. concentrated hydrochloric acid/96 ml. water) is heated at 95°C. for two and one-half hours. The solution is made alkaline with sodium carbonate and the precipitate is extracted into methylene chloride. The extract is dried, treated with charcoal and evaporated to dryness to give an oil which crystallizes upon standing, 5-benzyloxy-α-(N-t-butylamido)-6-methyl-2-pyridinemethanol, m.p. 140°–141°C.

This amide (4.0 g., 0.012 mol) in 75 ml. of tetrahydrofuran is stirred with 30 ml. of 1M diborane in tetrahydrofuran and refluxed for 18 hours. The reaction mixture is treated with methanol and ethereal hydrogen chloride, then evaporated to dryness. The residue is dissolved in water, washed with ether and the acidic solution is made alkaline with 10% sodium hydroxide solution. The basic solution is extracted with ether, the extract dried and evaporated to dryness to yield 5-benzyloxy-α-(t-butylaminomethyl)-6-methyl-2-pyridinemethanol, m.p. 96°–97°C.

Debenzylation is accomplished by hydrogenating a solution of the above prepared compound (1.25 g., 0.0040 mol) in 50 ml. of methanol over 1.0 g. of 10% palladium-on-carbon at 60 psi for 15 minutes. The catalyst is removed by filtration and the filtrate is evaporated to dryness to give an oil which crystallizes upon standing. This material is dissolved in ethanol and treated with a molar equivalent of fumaric acid. Addition of ether precipitates α-(t-butylaminomethyl)-5-hydroxy-6-methyl-2-pyridinemethanol fumarate, m.p. 218°C.

EXAMPLE 4

Following the procedures outlined in Example 1, 5-benzyloxy-6-methanesulfonylmethyl-2-pyridinecarboxaldehyde is reacted with cyclopentyl isocyanide to give upon hydrolysis 5-benzyloxy-α-(N-cyclopentylamido)-6-methanesulfonylmethyl-2-pyridinemethanol. Similar reduction with diborane followed by hydrogenation over palladium-on-carbon gives α-cyclopentylaminomethyl)-5-hydroxy-6-methanesulfonylmethyl-2-pyridinemethanol.

Similarly, employing cyclopropylmethyl isocyanide as described above yields the product α-(cyclopropylmethylaminomethyl)-5-hydroxy-6-methanesulfonylmethyl-2-pyridinemethanol.

Reacting 5-benzyloxy-6-methanesulfonylmethyl-2-pyridinecarboxaldehyde with 3,4-dimethoxyphenylisopropyl isocyanide and subsequent reduction of the amide intermediate and hydrogenation furnishes α-[2-(3,4-dimethoxyphenyl)-1-methylethylaminomethyl]-5-hydroxy-6-methanesulfonylmethyl-2-pyridinemethanol.

EXAMPLE 5

Following the procedures of Example 2, 5-benzyloxy-2-pyridinecarboxaldehyde is reacted with phenylisopropyl isocyanide to give upon acid hydrolysis 5-benzyloxy-α-(N-phenylisopropylamido)-2-pyridinemethanol which is reduced with diborane and the resulting amine is hydrogenated to yield 5-hydroxy-α-(2-phenyl-1-methylethylaminomethyl)-2-pyridinemethanol.

Similarly, reaction of the 5-benzyloxy-2-pyridinecarboxaldehyde with 3,4-dibenzyloxyphenylisopropyl isocyanide yields as the final product α-[2-(3,4-dihydroxyphenyl)-1-methylethylaminomethyl]-5-hydroxy-2-pyridinemethanol.

EXAMPLE 6

Following the procedures of Example 1, 5-benzyloxy-6-methanesulfonylmethyl-2-pyridinecarboxaldehyde is reacted with 4-benzyloxyphenylisopropyl isocyanide to furnish upon hydrolysis the intermediate amide which is first reduced to the amine with diborane and then hydrogenated over palladium-on-carbon to give 5-hydroxy-α-[2-(4-hydroxyphenyl)-1-methylethylaminomethyl]-6-methanesulfonylmethyl-2-pyridinemethanol.

Reacting 5-benzyloxy-6-methanesulfonylmethyl-2-pyridinecarboxaldehyde with 3,4-methylenedioxyphenylisopropyl isocyanide followed by reduction of the intermediate amide and hydrogenation of the amine gives 5-hydroxy-6-methanesulfonylmethyl-α-[2-(3,4-methylenedioxyphenyl)-1-methylethylaminomethyl]-2-pyridinemethanol.

EXAMPLE 7

Following the procedures of Example 3, 5-benzyloxy-6-methyl-2-pyridinecarboxaldehyde is reacted with 2-(4-benzyloxyphenyl)-1,1-dimethylethyl isocyanide to give upon hydrolysis the intermediate amide which is reduced with diborane followed by hydrogenation over palladium-on-carbon to give 5-hydroxy-α-[2-(4-hydroxyphenyl)-1,1-dimethylethylaminomethyl]-6-methyl-2-pyridinemethanol.

EXAMPLE 8

| Ingredients | Mg/Tablet |
|---|---|
| α-(t-butylaminomethyl)-5-hydroxy-6-methanesulfonylmethyl-2-pyridinemethanol* | 10 |
| Starch, U.S.P. | 15 |
| Lactose, U.S.P. | 150 |
| Magnesium Stearate, U.S.P. | 1 |

*added as the fumarate salt

A granulation of the above ingredients is compressed into tablets.

EXAMPLE 9

| Ingredients | Mg/Dose |
|---|---|
| α-(t-butylaminomethyl)-5-hydroxy-6-methanesulfonylmethyl-2-pyridinemethanol* | 0.125 |
| Alcohol, U.S.P. | 17 |
| Propellant (20% Freon 12/80% Freon 114 mixture) | 33 |

*added as the fumarate salt

The above ingredients in an aerosol dispensing system with a metered valve furnishes the indicated amounts per dose.

What is claimed is:

1. A chemical compound of the formula:

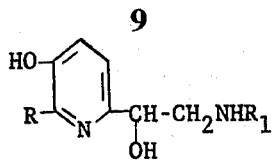

or a pharmaceutically acceptable acid addition salt of said compound, wherein:

R is hydrogen, methyl or methanesulfonylmethyl;

$R_1$ is branched chain lower alkyl of from 3 to 5 carbon atoms, cycloalkyl or cycloalkylmethyl, the cycloalkyl moiety having from 3 to 6 carbon atoms, or

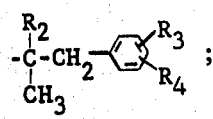

$R_2$ is hydrogen or methyl; and $R_3$ and $R_4$ are hydrogen, hydroxy, methoxy or, taken together in adjacent positions, methylenedioxy.

2. A compound according to claim 1 in which R is hydrogen or methyl.

3. A compound according to claim 2 in which R is hydrogen and $R_1$ is t-butyl, being the compound α-(t-butylaminomethyl)-5-hydroxy-2-pyridinemethanol.

4. A compound according to claim 2 in which R is methyl and $R_1$ is t-butyl, being the compound α-(t-butylaminomethyl)-5-hydroxy-6-methyl-2-pyridinemethanol.

5. A compound according to claim 1 in which R is methanesulfonylmethyl.

6. A compound according to claim 5 in which $R_1$ is t-butyl, being the compound α-(t-butylaminomethyl)-5-hydroxy-6-methanesulfonylmethyl-2-pyridinemethanol.

7. A compound according to claim 6 in the form of a free base.

8. A compound according to claim 6 in the form of a fumarate salt.

9. A compound according to claim 5 in which $R_1$ is 3,4-methylenedioxyphenylisopropyl, being the compound 5-hydroxy-6-methanesulfonylmethyl-α-[2-(3,4-methylenedioxyphenyl)-1-methylethylaminomethyl]-2-pyridinemethanol.

10. A pharmaceutical composition having β-adrenergic stimulant activity, in dosage unit form, comprising a pharmaceutical carrier and an effective amount of a chemical compound as defined in claim 1.

11. The method of producing β-adrenergic stimulant activity which comprises administering internally to animals in need thereof an amount sufficient to produce said activity of a chemical compound as defined in claim 1.

12. A pharmaceutical composition according to claim 10 in which the chemical compound is α-(t-butylaminomethyl)-5-hydroxy-6-methanesulfonylmethyl-2-pyridinemethanol.

13. The method according to claim 11 in which the chemical compound is α-(t-butylaminomethyl)-5-hydroxy-6-methanesulfonylmethyl-2-pyridinemethanol.

* * * * *